(12) United States Patent
Squirrell et al.

(10) Patent No.: US 8,609,375 B2
(45) Date of Patent: *Dec. 17, 2013

(54) METHOD FOR DETECTING VIABLE CELLS IN A SAMPLE BY USING A VIRUS

(75) Inventors: David James Squirrell, Wiltshire (GB); Martin Alan Lee, Wiltshire (GB)

(73) Assignee: Enigma Diagnostics LLC (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/276,772

(22) Filed: Oct. 19, 2011

(65) Prior Publication Data

US 2012/0141976 A1 Jun. 7, 2012

Related U.S. Application Data

(62) Division of application No. 11/816,331, filed as application No. PCT/GB2006/000551 on Feb. 16, 2006, now Pat. No. 8,071,337.

(51) Int. Cl.
*C12P 19/34* (2006.01)

(52) U.S. Cl.
USPC ........................................... 435/91.2

(58) Field of Classification Search
USPC ........................................... 435/91.2
See application file for complete search history.

(56) References Cited

U.S. PATENT DOCUMENTS

| | | | |
|---|---|---|---|
| 5,888,725 | A | 3/1999 | Sanders |
| 6,335,161 | B1 | 1/2002 | Martin et al. |
| 6,355,445 | B2 | 3/2002 | Cherwonogrodzky et al. |
| 6,660,470 | B1 | 12/2003 | Sanders |

FOREIGN PATENT DOCUMENTS

| | | |
|---|---|---|
| GB | 2338301 A | 12/1999 |
| WO | 9004041 A1 | 4/1990 |
| WO | 9722713 A1 | 6/1997 |
| WO | 9848042 A2 | 10/1998 |
| WO | 9928500 A1 | 6/1999 |
| WO | 9928501 A1 | 6/1999 |
| WO | 9942611 A1 | 8/1999 |
| WO | 02072776 A2 | 9/2002 |
| WO | 03035889 A2 | 5/2003 |
| WO | 2004036177 A2 | 4/2004 |
| WO | 2005001475 A2 | 1/2005 |
| WO | 2007066126 A1 | 6/2007 |

OTHER PUBLICATIONS

Hibma et al., "Infection and removal of L-forms of *Listeria monocytogenes* with bred bacteriophage", International Journal of Food Microbiology, 1997, pp. 197-207, vol. 34.
Jensen et al., "Prevalence of Broad-Host-Range Lytic Bacteriophages of *Sphaerotilus natans, Escherichia coli,* and *Pseudomonas aeruginosa*", Applied and Enviromental Microbiology, 1998, pp. 575-580, vol. 64, No. 2.
Meynell, "The Significance of Bacteriophage in Bacterial Classification. A Review", Journal gen. Microbiology, 1964, pp. 461-469, vol. 36.
Schuppli et al. "Altered 3'-terminal RNA structure in phage Qbeta adapted to host factor-less *Escherichia coli*", Proc. Natl. Acad. Sci. USA, 1997, pp. 10239-10242, vol. 94.
International Search Report for PCT/GB2006/000551 dated Aug. 30, 2007; 9 pages.
International Search Report for PCT/GB2006/000551 dated May 17, 2006; 13 pages.
Goodridge et al., "Reporter bacteriophage assays as a means to detect foodborne pathogenic bacteria", Food Research International, 2002, pp. 863-870; 35.
Loessner et al., "Construction of Luciferase Reporter Bacteriophage A5H::luxAB for Rapid and Sensitive Detection of Viable Listeria Cells", Applied and Environmental Microbiology, 1996, pp. 1133-1140, 62 (4).
Mole et al., "Phage as a diagnostic—the use of phage in TB diagnosis", Journal of Chemical Technology and Biotechnology, 2001, pp. 683-688, 76.
Search Report for GB0503172.9 dated Jul. 8, 2005; 1 page.
Applegate, B.M., et al., "Detection of Viable Foodborne Pathogens by Bacteriophage/ Bioluminescent Sensors," Food Science, Purdue University, CRIS No. 0188147, Project No. IND060046, undated, 2 pages.
Bright, N., et al., "A model system for pathogen detection using a two-component bacteriophage/bioluminescent signal amplification assay", Proceedings of the SPIE, (2004), vol. 5271, pp. 13-19.
Final Office Action for U.S. Appl. No. 11/816,331, dated Mar. 17, 2010, 11 pages.
Examiner Interview Summary for U.S. Appl. No. 11/816,331, dated Aug. 16, 2011, 3 pages.
Final Office Action for U.S. Appl. No. 11/816,331, dated Aug. 18, 2010, 16 pages.
Non-Final Office Action for U.S. Appl. No. 11/816,331, dated Sep. 1, 2009, 13 pages.
Notice of Allowance and Fees Due for U.S. Appl. No. 11/816,331, dated Sep. 20, 2011, 9 pages.

*Primary Examiner* — Cynthia B Wilder

(57) ABSTRACT

A method for detecting viable cells such as bacterial cells, within a sample, said method comprising (i) incubating said sample with a virus which is able to infect said cells under conditions which allow said virus to infect and replicate within any such cells which are viable; and (ii) detecting any nucleic acid obtained by replication of the virus in said cell.

6 Claims, 5 Drawing Sheets

METHOD FOR DETECTING VIABLE CELLS IN A SAMPLE BY USING A VIRUS

This application is a divisional application of U.S. patent application Ser. No. 11/816,331, now U.S. Pat. No. 8,071,337, filed Nov. 9, 2007, which is a 371 national stage application of PCT/GB06/000551, filed Feb. 16, 2006, each of which is hereby incorporated by reference in its entirety.

The entire contents of a paper copy of the "Sequence Listing" and a computer readable form of the sequence listing, entitled 091008_Seq_List.txt that is 1 kilobytes in size and created on Nov. 24, 2009, are herein incorporated by reference.

The present application relates to a method for detecting the presence of viable cells within a sample, as well as to kits for use in the method.

The rapid detection of bacteria and other organisms is very important in the field of public safety. It is particularly important in the food industry where it is essential that food and drinks are free from contamination by harmful bacteria and other microorganisms, for example *E. coli* 0157.

It is also very important in the field of veterinary and medical diagnostics that potentially harmful bacteria and other organisms are identified quickly, to allow infection to be controlled and to enable the correct treatment to be given to the animal or patient. It is also important that medical, cosmetic and veterinary preparations are free from harmful contaminants such as bacteria.

In addition some bacteria and other organisms, for example, *Bacillus anthracis* have potential for use as biological warfare agents. It is therefore important that the presence of such organisms in a sample can be tested for quickly. For example, it has been estimated that there is only a 6-hour window in which to administer effective treatment after the initial inhalation of *Bacillus anthracis* spores.

Several methods are currently available for detection of bacteria and other organisms.

For example traditional culture-based methods can be used to detect the presence of bacteria in a sample. However a problem commonly encountered in such assays is that the concentration of the organism in a sample is generally very low. Thus it may be necessary to incubate the sample for a significant period of time prior to conducting the assay in order to culture the organism to detectable levels. This delay may be unacceptable in many situations where public health is at risk.

Alternatively PCR and other nucleic amplification technologies provide a fast and sensitive DNA based means of detecting the presence of bacteria and other organisms. These techniques in general rely on the detection of bacterial DNA using amplification reactions such as the polymerase chain reaction (PCR).

However there are disadvantages associated with such amplification techniques because DNA is a very robust chemical species and can survive intact when the host cell is dead.

For example, if a poultry product has been contaminated with a pathogenic bacterium such as *Salmonella* and then cooked, the food will have been rendered safe. In a traditional culture-based method of detection the food will be shown to be safe but the method itself will take a long time to conduct, whereas a DNA method whilst quicker will show a false positive result because the *Salmonella* DNA will still be present in the sample.

Alternatively WO 2003/035889 describes a technique in which modified phage comprising marker sequences are used to detect viable cells. In this method the modified phage are introduced into a sample to be tested. If viable cells are present, then the phage can replicate using the cells machinery resulting in a detectable increase in the marker sequence.

However there are disadvantages associated with this technique.

Firstly the need to incorporate marker sequences necessarily increases the complexity of the test, since the phage have to be specifically engineered to contain the desired marker sequence. Such modified phage will therefore increase the cost and complexity of such tests.

In addition since the marker sequence is added to the sample to be tested, due to its presence in the phage, it is necessary to quantitatively detect any increase in the amount of this marker sequence in the sample. This means that the incubation period has to be long enough to ensure that false positive results are not generated.

There is therefore a need to provide a reliable test method for potential biological hazards, which can be operated easily, and reliably with a low level of false positive or negative results.

Accordingly the present invention provides a method for detecting viable cells within a sample, said method comprising (i) incubating said sample with a virus which is able to infect said cells under conditions which allow said virus to infect and replicate within any such cells which are viable; and (ii) detecting any nucleic acid obtained by replication of the virus in said cell.

By detecting nucleic acid obtained specifically by replication of the virus, it is possible to determine that there are viable cells present in the sample, as compared simply to dead cells.

In a particular embodiment the invention provides a method for detecting viable cells within a sample, said method comprising (i) incubating said sample with a virus which is able to infect said cells under conditions which allow said virus to infect and replicate within any such cells which are viable; and (ii) detecting any nucleic acid obtained by replication of the virus in said cell, provided that when the virus is a modified virus which has been modified to include a marker sequence, the nucleic acid detected is one which is uniquely produced on replication of the virus within the cell.

In order to ensure that any viable cells are infected during step (i), they may be subjected to a pre-conditioning step, for example by bringing them to an incubation temperature of for example 37° C.-42° C., for a suitable period of time, for example for 2.5-4.5 hours before addition of the virus. This may be particularly necessary if for instance, the sample contains stressed bacteria, for example as a result of storage or isolation procedures such as immunomagnetic separation (IMS) methods. They may then be held at the incubation temperature for a period of time to allow infection and some replication to occur.

The virus used may be a single stranded (ss) or double stranded (ds) RNA or DNA virus.

The nucleic acid detected in step (ii) may occur within the virus itself. In this case, it is necessary to quantitatively detect an increase in the amount of this nucleic acid in the sample. This method is advantageous over that described in WO 03/035889 since there is no need to modify the virus to include a marker sequence.

Preferably, however the nucleic acid detected in step (ii) is not contained within the virus itself, and is uniquely produced on replication of the virus within the cell. This means that the detection of any nucleic acid having this particular sequence would be indicative of the presence of viable cells within the sample, as they have been utilized in the production of the virus.

The virus may be either a wild type virus or a modified virus. When the virus is a modified virus which has been modified to include a marker sequence, the nucleic acid detected is one which is uniquely produced on replication of the virus within the cell.

In a particular embodiment the virus is not modified to include any marker sequence(s), for example target repeat sequences.

The virus may however be modified for other purposes, for example to increase the infectivity or specificity of the virus. Such viruses may be commercially available and therefore can provide advantages over naturally occurring viruses without significantly increasing the complexity or cost of the method, or they may be produced using conventional transformation methods.

The detection option which is selected will depend upon the particular virus being used.

In a particular embodiment, the virus is an RNA virus, in particular a single stranded RNA virus.

Particularly preferred single stranded RNA virus are Class VI RNA viruses, which comprise a single positive RNA strand. These viruses convert their RNA into complementary DNA (cDNA) using a process called reverse transcription. Converting RNA into cDNA enables the virus to replicate inside the host cell.

However, detection of the cDNA produced in step (ii) above, provides a unique indicator that viable cells, capable of being infected and sustaining a viral infection, are present within the sample.

The reverse transcriptase enzyme necessary for carrying out reverse transcription is an enzyme which is often present in the virion and therefore the virus does not need to rely on the host cell to provide this essential enzyme. However the host must provide many other factors that the virus needs to be able to infect and replicate within the host cell.

For example internalization of the virus into the host cell requires host factors such as surface proteins and cell membranes with which the virus must interact. In addition reverse transcription requires a stable milieu containing the necessary dNTP substrates to form cDNA from the viral RNA.

If the host cell is not viable and is therefore not producing the additional factors such as those described above, then the virus will not be able to infect and replicate within the host cell, and thereby generate detectable DNA which may for instance, form the target of an amplification reaction.

If the host cell is viable, the RNA virus will be able to infect and replicate within the host cell producing detectable cDNA. If the host cell is not viable then the virus will not be able to infect the host cell and/or replicate inside it and so no cDNA will be detectable.

In this embodiment of the invention, during step (i) it is necessary only to incubate the sample for a period long enough to ensure that at least one cDNA is produced by the host cell. That can then be detected using a conventional amplification reaction such as PCR. However incubation for a period long enough to produce multiple copies may also be carried out. Generally, incubation periods of from 30 minutes to 1 hour would be sufficient to generate detectable nucleic acid.

Alternatively, the virus may comprise a single negative strand RNA molecule, such as class V viruses. On infecting a viable host cell, the cell will produce a complementary positive RNA strand, specifically an mRNA strand. As described above however, this process can only take place within the stable milieu of an infected cell. The thus-produced positive RNA strand may then be detected using for example a conventional reverse transcriptase-PCR reaction (RT-PCR).

Preferably, the detection is carried out using a single primer in the RT step so that only a single complementary DNA molecule is produced.

In a particular embodiment, this cDNA is then detected by a conventional PCR amplification, designed to amplify a region within the cDNA. Digestion of the RNA strand prior to this amplification may be preferable in order to ensure that contamination is minimized.

Alternatively, an increase in the amount of viral nucleic acid itself can be used as an indicator of the presence of viable cells. Again, this is because replication of the virus can take place only within a viable cell. In this embodiment the nucleic acid to be detected is other than a reporter sequence, and is preferably a wild-type sequence.

For instance, where the virus is a DNA virus, such as a single stranded class II virus, or a double-stranded class I virus, it will generally be necessary to detect an overall increase in DNA following infection to determine that specifically viable cells are present within the sample. This can be done in various ways, but probably the most convenient would be to amplify the DNA using a quantitive PCR assay, such as the TAQMAN™ assay or the like.

Where the virus is an RNA virus, an increase in RNA may need to be detected, for instance using RT-PCR.

The sample to be tested in the method of the invention may be any sample, which is suspected of or known to contain prokaryotic cells and/or lower eukaryotic cells and/or higher eukaryotic cells.

Examples of samples included within the scope of this invention include, food samples, samples of human or animal bodily fluids or tissues and in particular clinical samples, medicinal, cosmetic or veterinary preparations or medications, plant samples, soil samples, air samples, water samples and cell culture samples. Most preferably the sample is a food sample.

This method of the invention can be applied to detect viable examples of any cell that a virus is capable of infecting. These include prokaryotic and eukaryotic cells. The cells may be for example microorganisms, such as bacteria. Particular examples of bacteria which may be detected include *E. coli, Salmonella, Listeria, Campylobacter, Legionella, Mycobacterium, Staphylococcus* or *Streptococcus*.

Alternatively the cells may be contained within small organisms, such as insects, plants or fungi.

Additionally they may be present in cells or cell lines including mammalian cell lines, plant and fungal cell lines. Detection of viable cells in cell lines is frequently carried out, for instance during the screening of pharmaceutical or other reagents, or in biological analysis, and the method described herein may be useful in this context.

The method may be particularly useful for example in analyzing cell containing samples from patients who have been treated for a particular bacterial infection with antibiotics. Appropriate samples taken from these patients can be tested in accordance with the method described herein to determine whether the antibiotic treatment has been effective or not.

The virus can be either a wild type virus or a recombinant virus. If the cell is viable, the virus will be able to infect it and replicate, either in the case of positive RNA, by producing a cDNA, or in other cases by producing more RNA, and in particular mRNA. Where a modified virus is used detection of the complementary sequence of for example an introduced marker sequence uniquely produced on replication of the of the virus within the cell, may then provide a clear indication of the presence of viable cells. Suitable marker sequences may include antibiotic resistance genes.

The method described above is general in nature in that it can be used to detect the viability of any type of cell, which may be infected by a virus. For example if a sample needs to be tested for viable *E. coli* 0157 cells any virus capable of infecting *E. coli* 0157 cells could be used.

In some samples for example a milk or soil sample, the number of types of bacteria or other cells present may be very high. Testing for the viability of a particular type of cell in such samples is understandably difficult. However in a preferred embodiment of this invention the virus used is specific to the type of cell, the presence of which, in viable form, is under investigation. In other words in this embodiment the virus used must only be capable of infecting and replicating within the cell type under investigation.

For instance, a known coliphage is obtainable from the National Collection of Industrial and Marine Bacteria, Aberdeen, UK, as NCIMB 10359. The Felix 01 phage obtainable from Diagnostics Pasteur (Sanofi) Watford UK is capable of infecting *Salmonella* strains, in particular *Salmonella* Newport.

In this preferred embodiment the specific virus used, will only produce detectable nucleic acid if the cell being tested for is present and viable no matter how may other types of bacteria or other cells are present. This advantageously means that the cells to be tested do not have to be isolated before their presence in viable form can be determined.

Viruses may be used singly or as multi-specificity mixtures, where the viability of more than one cell is being looked for. In the latter case, detection of multiple nucleic acid sequences, such as cDNA sequences, each characteristic of individual viruses is carried out subsequently.

The infection and replication cycle of viruses will often result in an infected cell bursting and releasing its contents. If this is the case, the nucleic acid detected in step (ii) of the method described above can be detected without actively lysing or homogenizing the cells. However lysis or homogenization of any cells within the sample can be carried out before step (ii) if desired or necessary.

Lysis or homogenization can be affected using any conventional method, for instance, by heating or example to 94° C., sonication or by addition of a lytic agent such as a detergent.

In a preferred embodiment, where for example a cDNA produced by the virus or a DNA derived from a replicated RNA is detected in step (ii), this is preferably achieved using an amplification reaction, for example a polymerase chain reaction (PCR). In this case, reagents, including primers, polymerases, nucleotides, and buffers as are well known, are added at the end of step (i) after lysis of the cells if necessary, and then subjected to thermal cycling as is conventional, in order to amplify any target DNA present.

The amplification product may then be detected using conventional methods such as gel electrophoresis, followed by visualization using dyes.

Preferably the amplification reaction is carried out in such a way that the amplification product generates a detectable signal, and in particular a visible signal, for example a fluorescent signal, as it progresses. Many assay formats that produce such signals are known in the art. They may utilize reagents such as DNA binding agents such as intercalating dyes which emit radiation and particularly fluorescent radiation at greater intensity when they are intercalated into DNA, as well as probes and primers which include fluorescent labels, arranged to undergo fluorescent energy transfer (FET) and particularly fluorescent resonant energy transfer (FRET).

There are two commonly used types of FET or FRET probes, those using hydrolysis of nucleic acid probes to separate donor from acceptor, and those using hybridization to alter the spatial relationship of donor and acceptor molecules.

Hydrolysis probes are commercially available as Taq-Man™ probes. These consist of DNA oligonucleotides that are labelled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibits 5' to 3' exonuclease activity. TaqMan™ probes are protected at the 3' end by phosphorylation to prevent them from priming Taq extension. If the TaqMan™ probe is hybridized to the product strand, an extending Taq molecule may also hydrolyze the probe, liberating the donor from acceptor as the basis of detection. The signal in this instance is cumulative, the concentration of free donor and acceptor molecules increasing with each cycle of the amplification reaction.

Hybridization probes are available in a number of forms. Molecular beacons are oligonucleotides that have complementary 5' and 3' sequences such that they form hairpin loops. Terminal fluorescent labels are in close proximity for FRET to occur when the hairpin structure is formed. Following hybridization of molecular beacons to a complementary sequence the fluorescent labels are separated, so FRET does not occur, and this forms the basis of detection.

Pairs of labelled oligonucleotides may also be used. These hybridize in close proximity on a PCR product strand-bringing donor and acceptor molecules together so that FRET can occur. Enhanced FRET is the basis of detection. Variants of this type include using a labelled amplification primer with a single adjacent probe.

Other methods for detecting amplification reactions as they occur are known however, and any of these may be used. Particular examples of such methods are described for example in WO 99/28500, British Patent No. 2,338,301, WO 99/28501 and WO 99/42611.

WO 99/28500 describes a very successful assay for detecting the presence of a target nucleic acid sequence in a sample. In this method, a DNA duplex binding agent and a probe specific for said target sequence is added to the sample. The probe comprises a reactive molecule able to absorb fluorescence from or donate fluorescent energy to said DNA duplex binding agent. This mixture is then subjected to an amplification reaction in which target nucleic acid is amplified, and conditions are induced either during or after the amplification process in which the probe hybridizes to the target sequence. Fluorescence from said sample is monitored.

An alternative form of this assay, which utilizes a DNA duplex binding agent which can absorb fluorescent energy from the fluorescent label on the probe but which does not emit visible light, is described in co-pending British Patent Application No. 223563.8. Any of these assays may be used in the context of the method of the invention in order to detect the target cDNA sequence.

Many of these assays can be carried out in a quantitative manner as is well known in the art, for example by monitoring the signal from the amplification mixture at least once during each cycle of the amplification reaction.

By carrying out the reaction in this way, the amount of nucleic acid present in the sample may be determined. This may be related to the amount of viable cells in the original sample, or it may be used to determine an increase in the amount of the nucleic acid as a result of viral replication within viable cells.

As stated above the particular nucleic acid detected may be any characteristic sequence, which is produced or replicated as a result of viral infection of viable cells. Where single specificity viruses are used in the assay, this may be any sequence derived from the virus, or any other sequence introduced into a recombinant virus during its preparation. When the virus is a modified virus which has been modified to include a marker sequence, the nucleic acid is one which is uniquely produced on replication of the virus within the cell.

Where multi-specificity mixtures of viruses are used in the method, then it is necessary to detect nucleic acid sequences, which are characteristic sequences transcribed from each of the viruses used in order to determine whether specific types of cells in the sample are viable. In this case therefore, it may be desirable to detect sequences which are uniquely produced on replication of the virus within the cell and correspond to specifically introduced marker sequences in each virus used.

In this case, where the sequences detected are DNA sequences, multiplex PCR reactions using different signalling reagents or systems may be employed in order to detect the various sequences which are produced. This may be achieved, for example by labelling probes or primers used in the amplification reaction using different labels, for example, labels which fluoresce at different wavelengths. Examination of the signal from each label, for example at each of the different wavelength, is then carried out, if necessary with appropriate signal resolution where the wavelengths overlap.

Where, in the method of the invention, the nucleic acid being detected is present in the virus itself, it is only an increase in the amount of that nucleic acid which can be used to indicate the presence of viable cells. Therefore, in step (ii) the sample is tested to detect any increase in the concentration of that nucleic acid sequence. An increase in the amount of the target nucleic acid sequence is indicative of the presence of a viable host cell within the sample. Whereas no increase in the amount of the target nucleic acid is indicative of the fact that there are no viable host cells in the sample being tested.

In this embodiment, it may be desirable to extract a sample from the mixture formed by addition of virus to sample, prior to incubation, and the amount of nucleic acid within this extracted sample tested, to provide a baseline for comparison. Additional extracted samples may be alternatively or additionally taken at any time during incubation.

Most preferably the amount of nucleic acid present before and after incubation is determined by a suitable method. For instance, DNA concentrations may be detected using quantitative amplification reactions, such as quantitive PCR, although other methods for detecting DNA which do not involve amplification may also be used. RNA concentrations may be detected using RT-PCR, combined if appropriate with PCR reactions to detect the thus produced DNA.

The pre-incubation sample and post-incubation sample must be treated in the same manner so that the results can be directly compared. Most preferably a water control is also used.

A further aspect of the invention provides a kit for carrying out the methods described above. The kit suitably contains a virus, and one or more reagents necessary for detecting a nucleic acid.

In a preferred embodiment the kit contains a virus, and one or more reagents necessary for detecting nucleic acid obtained by replication of the virus in said cell, provided that when the virus is a modified virus which has been modified to include a marker sequence, the one or more reagents are necessary for detecting a nucleic acid which is uniquely produced on replication of the virus within the cell.

Most preferably the virus is a bacteriophage however other DNA or RNA virus, which is capable of infecting lower and/or higher eukaryotic cells may be used depending upon the nature of the cells under test.

Where the virus used is an RNA virus, this is preferably at least partially but preferably fully purified of contaminating DNA before step (i). Such viruses form a further aspect of the invention.

Suitably the kit may comprise an RNA virus and one or more reagents for detecting cDNA obtainable by reverse transcription of a sequence within said RNA virus. Most preferably the said one or more reagents comprises a pair of primers which are specific for any cDNA obtainable by reverse transcription of a sequence within said RNA virus.

Alternatively the kit may comprise a DNA virus and one or more reagents suitable for quantitatively detecting DNA. Most preferably the said one or more reagents comprises a pair of primers which are specific for a DNA sequence in the virus.

Alternatively kits may comprise reagents such as primers, which are required to conduct an RT-PCR reaction to detect an RNA.

Possible additional elements of the kits comprise other reagents suitable for use in the detection of the nucleic acid sequences. In particular, the kit may comprise intercalating dyes, or probes for use the detection of any nucleic acids produced using the methods described above.

The primers may suitably be labelled in such a way that the amplification product is directly detectable. For example, they may include fluorescent or other labels as described above.

Additionally or alternatively, the kits may include probes, which are specific for the amplification product and which are labelled to assist in detection of product. They may comprise single- or dual-labelled hydrolysis or hybridization probes. When appropriate they may include intercalating dyes or other DNA duplex binding agents, which form elements of the detection system.

The invention will now be particularly described by way of example with reference to the accompanying diagrammatic drawings in which.

Figure 4:
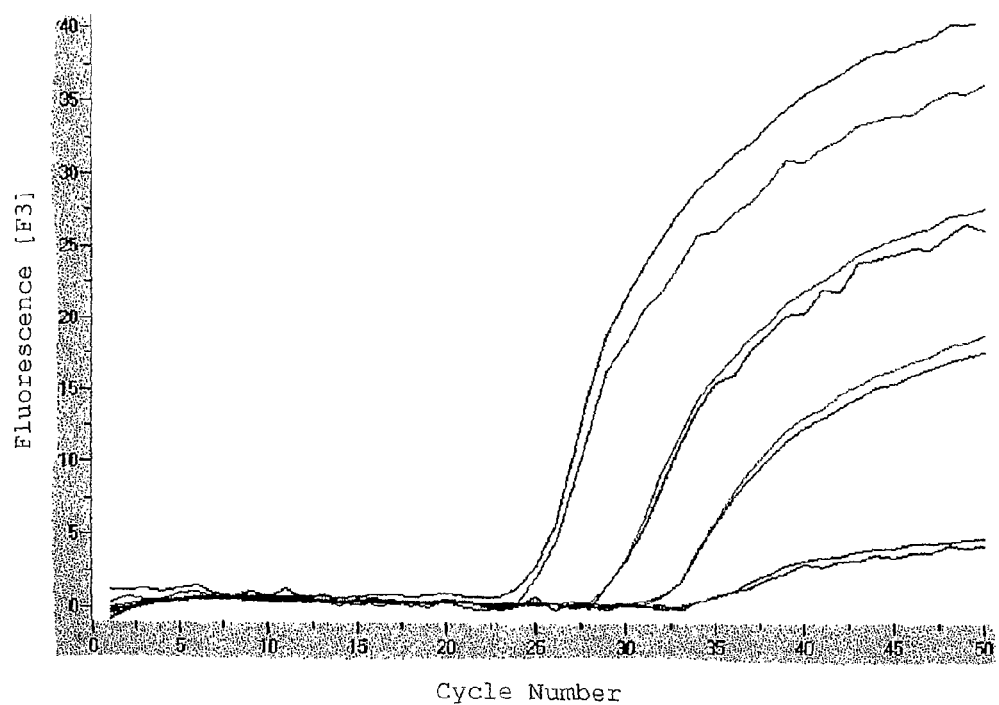
Figure 5:
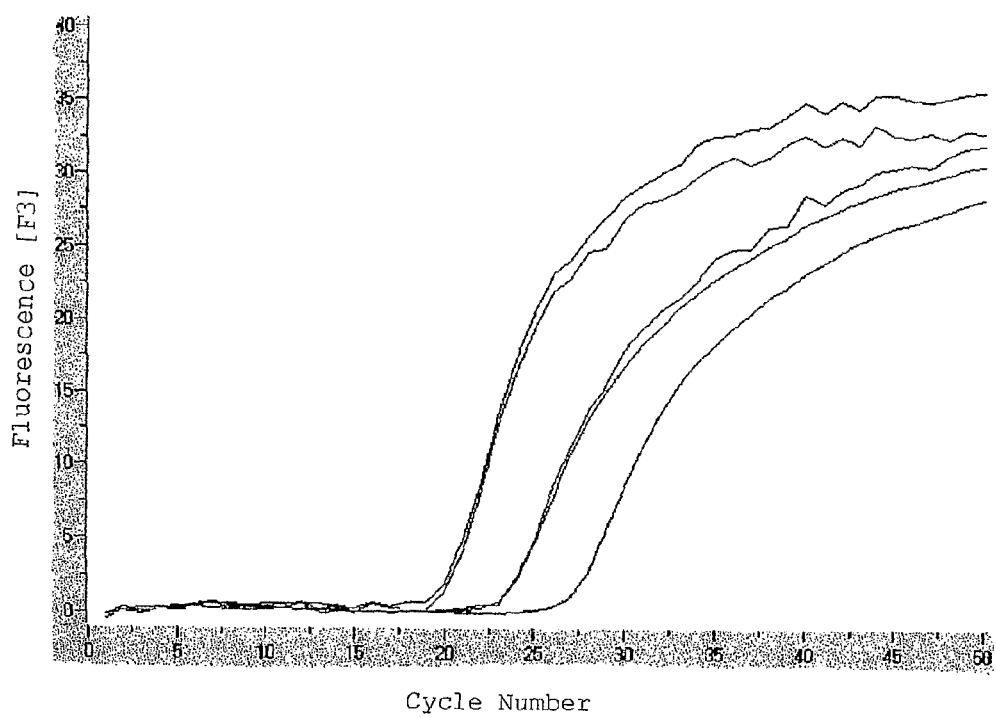

FIG. 4 illustrates the results of an amplification of any cDNA using a reverse primer showing that amplification was detected at approximately cycle 25, 29, 32 and 34 for the neat, 1:10, 1:100 and 1:1000 test sample respectively; and FIG. 5 illustrates the results of an amplification of cDNA using both forward and reverse primers, showing that amplification was detected at approximately cycle 20, 23, 27 for the neat, 1:10 and 1:100 test sample respectively.

EXAMPLE 1

Figure 1:
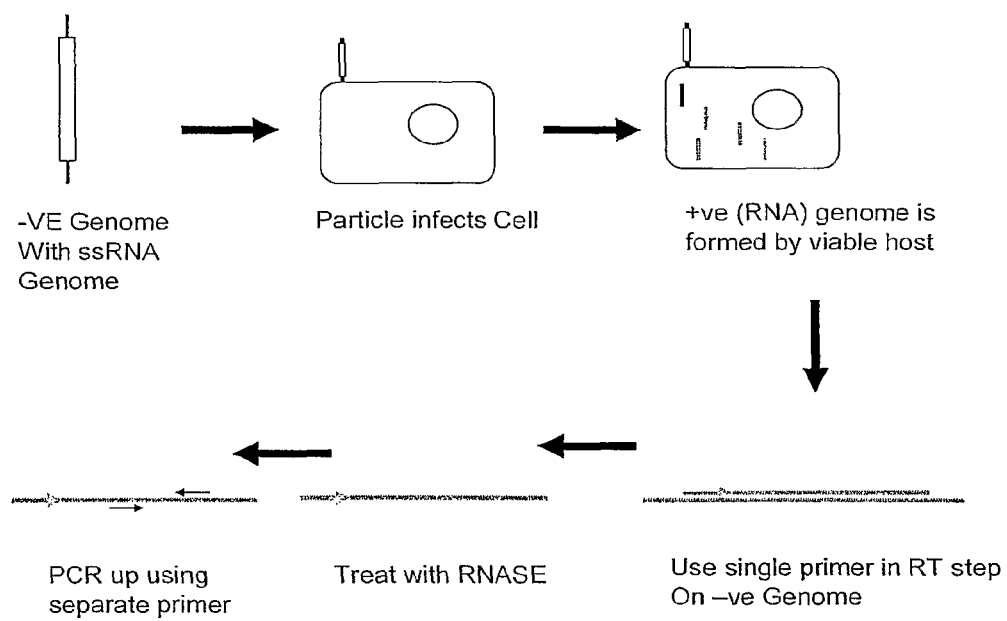
FIG. 1 illustrates schematically, a detection method according to the invention.

In the embodiment illustrated in FIG. 1, a class V virus preparation, having a single stranded negative genome is applied to a sample.

The sample may be any suitable sample but may comprise a bacterial extract in broth or phosphate-buffered saline (PBS), wherein the bacteria are not stressed and therefore receptive to infection. Samples will be diluted if necessary, for example so that they may contain from $6 \times 10^6$ to $2 \times 10^3$ cells $ml^{-1}$.

Virus preparations are suitably previously treated to remove contaminating DNA, for instance, by treatment with a DNAse enzyme. They may also be purified by centrifugation, with resuspension in for example buffered peptone water (BPW), for form phage titres of for instance $10^{10}$ $ml^{-1}$.

These preparations, for instance about 20 μl phage, are then added, followed by gentle mixing for 30 seconds. Thereafter the mixture is suitably allowed to stand for 5 minutes to encourage phage attachment.

Incubation is then suitably carried out, for example in a water bath at 37° C. for 30 minutes, during which the cultures may be gently stirred.

During this period, phage will infect viable cells (as illustrated) and multiple copies of positive RNA are generated within those cells.

At the end of this procedure, if necessary the cells are lysed, for example by heating them to 94° C., and the resultant mixture subjected to an RT-PCR to generate the complementary DNA sequence from the positive RNA. This is suitably done using a single primer, which is specific for the positive RNA.

Example of typical conditions in a murine reverse transcriptase or AMV reaction are as follows:

Buffer: 10 mM Tris.HCl pH 8.3 (room temp), 1-6 mM $MgCl_2$, 0.1% Gelatin (optional), 10-50 mM KCl, BSA Fraction V 1-100 μg/ml;
Nucleotides: 50-400 μM;
Primers: random hexanucleotides, specific primers (as in PCR), or polydT primers (string of "T's"), 0.1-1 μM;
Enzyme: 0.25-5 units/μl (depending upon enzyme); and
Optional placental RNAse inhibitor, 1-20 units.

Treatment of the product with an RNAse will digest the RNA template leaving only the cDNA, which can be amplified and detected using a conventional PCR reaction.

All these steps are quick and therefore provide a rapid assay for detecting viable cells.

EXAMPLE 2

Strand-Selective MS2 RT-PCR Experiment

This experiment was conducted to show that cDNA can be produced and detected using strand directed RT-PCR. Specifically the experiment investigated strand-specific two-step RT-PCR in MS2 bacteriophage. The cDNA was made using the forward primer and reverse primer separately and using both combined. As only one type of RNA is present in the MS2, only one of the primers (e.g. Forward or Reverse) was expected to produce DNA that would amplify in a PCR.

Methods.

The primer and probe sequences used in the experiment indicated in Table 1. Both primers were diluted with DEPC treated $H_2O$ to a concentration of 10 μM. The probes were also diluted on to a concentration of 2 μM. The first probe was diluted with 0.1×TE and the second probe was diluted with DEPC treated $H_2O$.

TABLE 1

MS2 Primers and Probes

| Name | Sequence (5' to 3') | Length | Modification |
|---|---|---|---|
| Forward Primer | TCG TCG ACA ATG GCG GAA CTG (SEQ ID NO: 1) | 21 | None |
| Reverse Primer | CTT TAG GCA CCT CGA CTT TGA TGG (SEQ ID NO: 2) | 24 | None |
| First Probe | AGC TCT AAC TCG CGT TCA CAG GCT TAC AAA GTA ACC TGT T (SEQ ID NO: 3) | 40 | 3' FAM |
| Second Probe | GTT CGT CAG AGC TCT GCG CAG AAT CGC AAA TAT (SEQ ID NO: 4) | 33 | 5'Cy5 & 3' Phosphate |

For the RT-step, three reaction mixes were prepared using the concentration of reagents in Table 2:

TABLE 2

Reagents used in the RT step.

| Reagents | Lot No. | Stock Concentration | Amount added (μl) F & R Primers | F Primer | R Primer | Final Concentration |
|---|---|---|---|---|---|---|
| Reaction buffer | 1009 | 5X | 16 | 16 | 16 | 1X |
| dUTPs | 24/11 | 2 mM | 20 | 20 | 20 | 0.5 mM |
| Forward Primer | — | 10 μM | 10 | 10 | 0 | 1.25 μM* |
| Reverse Primer | — | 10 μM | 10 | 0 | 10 | 1.25 μM* |

*if added

The RT reaction mixes were made up to 71 μl with DEPC treated $H_2O$. Next, 8 μl of MS2 (at concentration $4 \times 10^9$/ml) was added to each tube. The samples were mixed and divided into two tubes containing 35 μl each, and denatured at 90° C. for 10 min. The tubes were then placed on ice and 0.5 μl of the RT enzyme MMuLV (60 units/μl, lot #173) was added to each tube. The samples were mixed gently and placed in a 48° C. water bath for 30 min for the transcription of cDNA.

The following test samples were prepared in duplicate for PCR analysis:
DEPC-treated $H_2O$, negative control (ntc)
4×10-fold dilution series of the cDNA made using the Forward primer
4×10-fold dilution series of the cDNA made using the Reverse primer
3×10-fold dilution series of the cDNA made using both primers
MS2 Purified DNA Product 1:1000 dilution, positive control PCR reaction mixes were prepared using a Corbett robot. The concentrations of reagents in each reaction are listed in Table 3.

TABLE 3

Concentration of reagents used in the PCR mix.

| Reagents | Lot # | Stock Concentration | Amount added (µl) per sample | Final Concentration |
|---|---|---|---|---|
| Tris Buffer pH 8.8 | 0016 | 0.5M | 2 | 50 mM |
| BSA | B8667 | 20 mg/ml | 0.25 | 0.25 mg/ml |
| MgCl$_2$ | 019 | 100 mM | 0.6 | 3 mM |
| dUTPs | 24/11 | 2 mM | 2 | 0.2 mM |
| First Probe | — | 2 µM | 2 | 0.2 µM |
| Second Probe | — | 2 µM | 2 | 0.2 µM |
| Forward Primer | — | 10 µM | 2 | 1 µM |
| Reverse Primer | — | 10 µM | 2 | 1 µM |
| Taq Antibody | GC102TA/7 | 5 units/µl | 0.16 | 0.04 units/µl |
| Taq Polymerase | 14/4 | 5 units/µl | 0.16 | 0.04 units/µl |

The PCR mix (18 µl) was added to a LightCycler capillary along with 2 µl of test sample. The capillaries were capped and spun briefly to 3000 rpm.

The following program was carried out on a LightCycler 1.0 (Roche): Amplification (50 cycles) of Denature at 95° C. for 5 s; Annealing at 55° C. for 20 s (Single fluorescent reading); Extension at 74° C. for 5 s; Melt (1 cycle); Hold at 50° C. for 15 s, Temp. Ramp at 95° C. at 0.1° C./s (Continuous fluorescent reading).

Data were analyzed using the LightCycler Data Analysis program.

Figure 2:
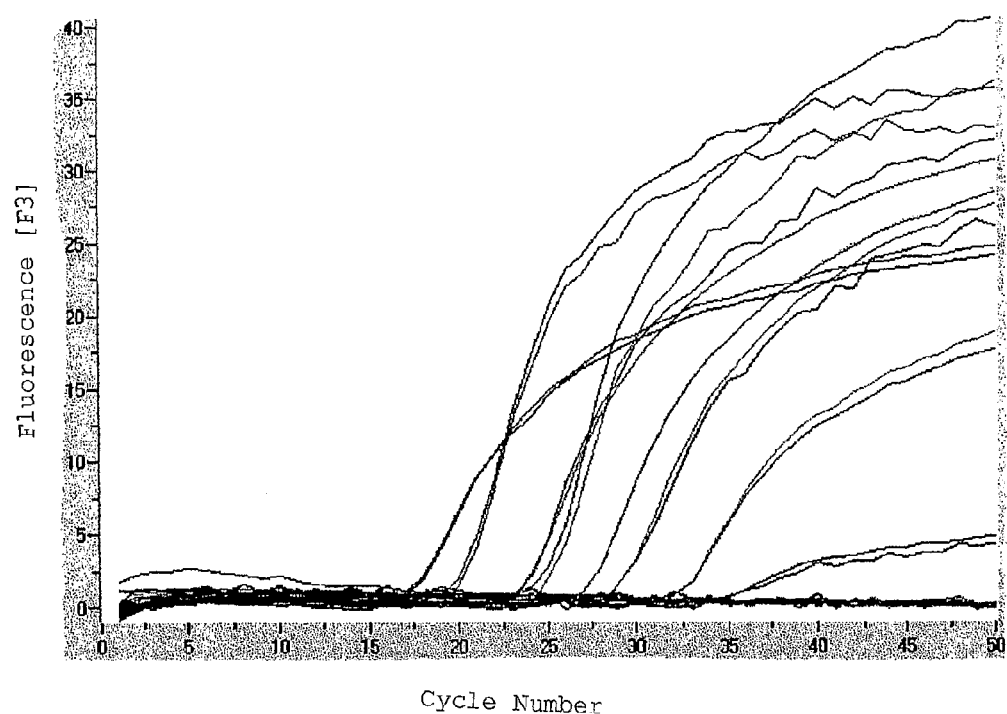
FIG. 2 illustrates amplification curves for all test samples in Example 2 hereinafter.
Figure 3:
FIG. 3 illustrates the results of an attempted amplification of any cDNA using a forward primer showing that none of the test samples produced amplified cDNA.

The results are shown in FIGS. 2 to 5. FIG. 2 shows the results for all test samples. FIG. 3 shows the results for test samples containing the forward primer. FIG. 4 shows the results for test samples containing the reverse primer. FIG. 5 shows the results for test samples containing both primers.

Summary of Results:

Using the Forward primer resulted in insufficient cDNA for detection in PCR. However, the Reverse primer produced sufficient cDNA for detection in PCR. When both primers were used cDNA was amplified with greater efficiency and detected earlier in PCR amplification.

Thus it has been demonstrated that a cDNA uniquely produced by reverse transcription of an RNA can be specifically detected using strand directed RT-PCR.

The invention claimed is:

1. A method for detecting viable bacterial cells within a sample, the method comprising:
   i) incubating the sample with a wild type virus specific for the cells, under conditions which allow the virus to infect and replicate within any such cells which are viable;
   ii) detecting an increase in the amount of a nucleic acid obtained by replication of the virus in the cells using quantitative Polymerase Chain Reaction; and
   iii) correlating the increase in the nucleic acid detected in step (ii) with the presence of the viable bacterial cells in the sample.

2. The method of claim 1 wherein the virus is a DNA or RNA virus and the nucleic acid detected in step (ii) occurs within the virus.

3. The method of claim 1, wherein before detection in step (ii) any intact cells within the sample are lysed.

4. The method of claim 1, wherein the sample is a food or clinical sample.

5. The method of claim 1, wherein the virus is a bacteriophage.

6. The method of claim 1, wherein the cell is an *E. coli, Salmonella, Listeria, Campylobacter, Legionella, Mycobacterium, Staphylococcus* or *Streptococcus*.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Primer sequence

<400> SEQUENCE: 1
tcgtcgacaa tggcggaact g                                       21

<210> SEQ ID NO 2
<211> LENGTH: 24
<212> TYPE: DNA
<213> ORGANISM: Artificial
<220> FEATURE:
<223> OTHER INFORMATION: Primer sequence

<400> SEQUENCE: 2
ctttaggcac ctcgactttg atgg                                    24

<210> SEQ ID NO 3
<211> LENGTH: 40
<212> TYPE: DNA
<213> ORGANISM: Artificial
<220> FEATURE:
<223> OTHER INFORMATION: Probe sequence

<400> SEQUENCE: 3
agctctaact cgcgttcaca ggcttacaaa gtaacctgtt                   40

```
<210> SEQ ID NO 4
<211> LENGTH: 33
<212> TYPE: DNA
<213> ORGANISM: Artificial
<220> FEATURE:
<223> OTHER INFORMATION: Probe sequence

<400> SEQUENCE: 4
gttcgtcaga gctctgcgca gaatcgcaaa tat                              33
```